United States Patent

Springs

[11] Patent Number: 6,059,834
[45] Date of Patent: *May 9, 2000

[54] SUSPENDED/ORTHOPAEDIC SLEEVES WITH INTERNAL ADHESIVE TO PREVENT SLEEVE MIGRATION

[75] Inventor: Michael A. Springs, Leawood, Kans.

[73] Assignee: Ortho-Care, Inc., Raytown, Mo.

[*] Notice: This patent issued on a continued prosecution application filed under 37 CFR 1.53(d), and is subject to the twenty year patent term provisions of 35 U.S.C. 154(a)(2).

[21] Appl. No.: 08/851,405

[22] Filed: May 5, 1997

Related U.S. Application Data

[63] Continuation of application No. 08/490,306, Jun. 14, 1995, abandoned.

[51] Int. Cl.$^7$ .................................................. A61F 2/78
[52] U.S. Cl. ................................................ 623/32; 602/63
[58] Field of Search ................................ 623/32–37, 57; 602/63, 62; 2/24

[56] References Cited

U.S. PATENT DOCUMENTS

| | | | |
|---|---|---|---|
| 2,244,871 | 6/1941 | Guinzburg | 2/59 |
| 2,653,601 | 9/1953 | Morrison | 602/62 |
| 3,322,873 | 5/1967 | Hitchcock | 264/222 |
| 3,934,583 | 1/1976 | Hollingshead | 602/62 |
| 4,146,021 | 3/1979 | Brosseau | 602/62 X |
| 4,492,227 | 1/1985 | Senn et al. | 602/63 |
| 4,635,626 | 1/1987 | Lerman | 602/61 |
| 4,790,855 | 12/1988 | Jolly | 623/32 |
| 4,822,371 | 4/1989 | Jolly et al. | 623/32 |
| 4,832,010 | 5/1989 | Lerman | 602/63 |
| 4,908,037 | 3/1990 | Ross | 623/32 |
| 4,961,418 | 10/1990 | McLaurin-Smith | 602/63 X |
| 5,007,937 | 4/1991 | Fishman et al. | 623/34 |
| 5,382,223 | 1/1995 | Springs . | |
| 5,497,513 | 3/1996 | Arabeyre et al. | 2/240 |
| 5,728,167 | 3/1998 | Lohmann | 623/36 |

FOREIGN PATENT DOCUMENTS

| | | | |
|---|---|---|---|
| 3832438 | 10/1989 | Germany | 602/62 |
| 2111833 | 7/1983 | United Kingdom | 602/63 |
| 2241647 | 9/1991 | United Kingdom | 602/62 |

*Primary Examiner*—David H. Willse
*Attorney, Agent, or Firm*—Hovey, Williams, Timmons & Collins

[57] ABSTRACT

Improved orthopaedic supports (10) and prosthesis suspension devices (36) are provided in the form of tubular bodies (12, 42) formed of resilient, stretchable material and configured to fit about a human limb. The inner surfaces (32) of the tubular bodies (12, 42) have anti-slip material (24, 26, 50) applied thereto. The anti-slip material (24, 26, 50) is preferably a synthetic resin material having a coefficient of static friction greater than that of the inner surfaces (32).

9 Claims, 1 Drawing Sheet

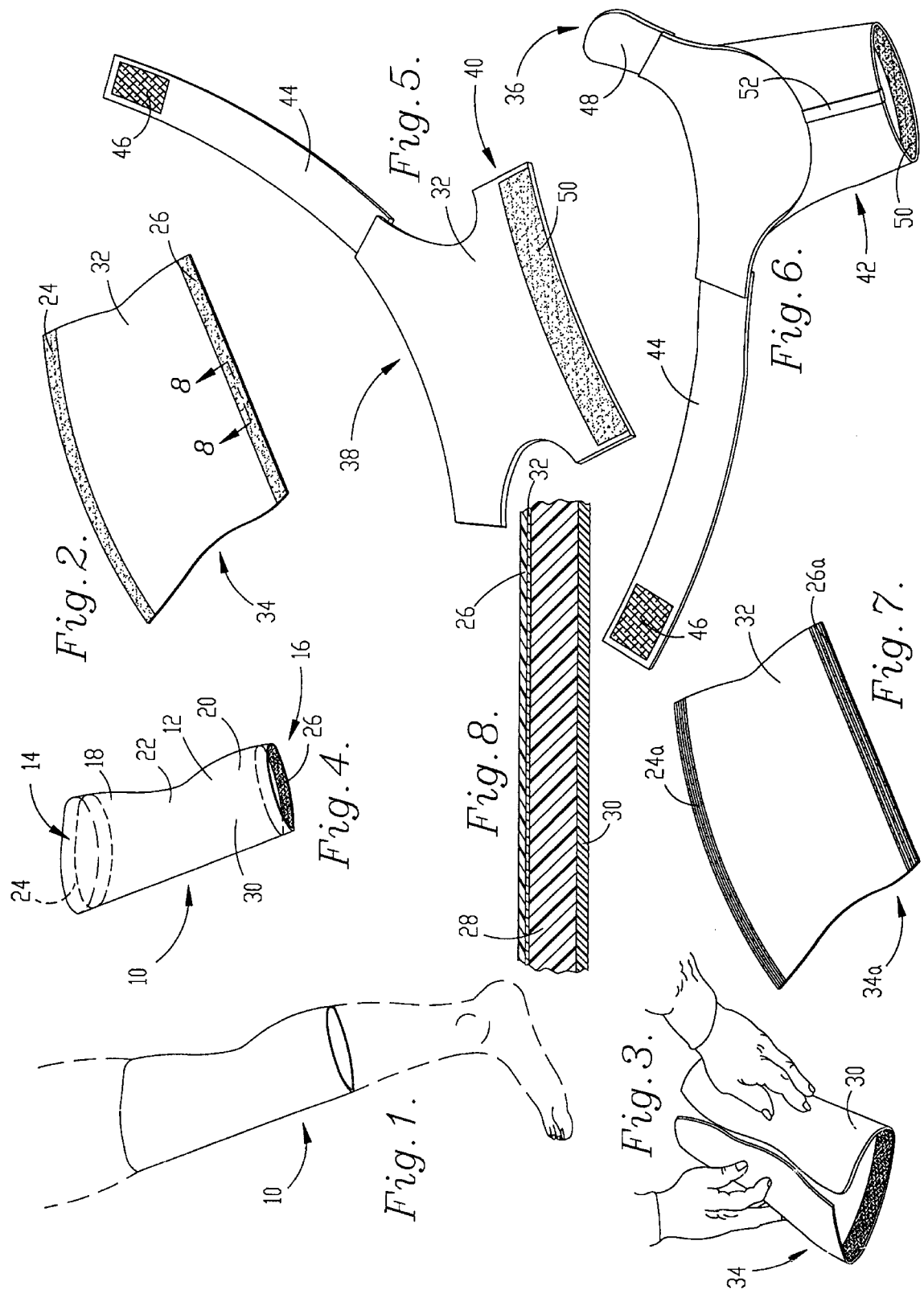

SUSPENDED/ORTHOPAEDIC SLEEVES WITH INTERNAL ADHESIVE TO PREVENT SLEEVE MIGRATION

This application is a continuation of application Ser. No. 08/490,306 filed Jun. 14, 1995.

BACKGROUND OF THE INVENTION

1. Field of the Invention

The present invention is broadly concerned with improved sleeve assemblies useful for orthopaedic or prosthetic suspension purposes. More particularly, it is concerned with sleeve assemblies of this type which include anti-slip material applied to a portion of the inner surfaces thereof in order to minimize migration or slippage of the sleeve assemblies in use.

2. Description of the Prior Art

Tubular orthopaedic supports of various types have long been used by individuals to support a weak or injured limb during rehabilitation or as a general protective measure. To give but one example, tubular knee supports are commonly used by athletes and include an elongated, sleeve-like tubular body adapted to be placed over the knee, lower thigh and upper calf regions of the leg. Such devices are typically fabricated of closed cell neoprene rubber material which may be lined with a soft terry or nylon fabric.

Prosthesis suspension devices used by amputees to support a limb prosthesis are also well known. Generally speaking, these devices include a tubular sleeve member adapted to fit around the limb at the region of the amputation, for the purpose of engaging and at least partially holding the prosthesis in position adjacent the limb stump. In the case of leg prosthesis supports, a belt is typically provided as a part of the overall device which extends around the waist of the wearer to provide additional support and strength. Prosthesis suspensions units of this character are also commonly made of faced neoprene rubber material.

A very significant problem with prior orthopaedic sleeves or prosthesis suspension devices is the tendency of these units to migrate or shift, particularly during walking other exercise. In the case of orthopaedic supports, these can fall or migrate a significant distance, particularly during athletic activity. By the same token, prosthesis suspension devices can slip or allow the prosthesis to move and shift to an unacceptable degree.

In response to these problems, it has been known to form the sleeve assemblies using neoprene rubber material having only the outer surface thereof faced with fabric, leaving an inner skin-engaging neoprene rubber surface. This has been done in an attempt to increase the resistance of these devices to migration or slippage. However, this expedient causes problems in its own right. First of all, unfaced neoprene rubber tends to erode and wear out quickly. Moreover, neoprene rubber causes skin irritation in a significant number of patients.

There is accordingly a real and unsatisfied need for improved sleeve assemblies useful in the context of orthopaedic supports or prosthesis suspension devices which largely eliminates the problems associated with sleeve migration, slippage and/or inadequate holding power.

SUMMARY OF THE INVENTION

The present invention overcomes the problems outlined above, and provides improved sleeve assemblies which are especially designed to give significantly enhanced resistance to slippage and migration. Broadly speaking, the sleeve assemblies of the invention are adapted to be worn on a limb and are in the form of tubular bodies formed of resilient, stretchable material. An anti-slip material is applied to a portion of the inner surfaces of the bodies and has a coefficient of static friction which is greater than that of the corresponding inner surfaces.

In preferred forms, the anti-slip material is applied as an essentially continuous band adjacent at least one end of the sleeve assembly, or as a plurality of thin, spaced apart bands. The anti-slip material is advantageously a synthetic resin which can be bonded adequately to the inner surfaces of the sleeve assemblies. Most preferably, a silicon-based synthetic resin adhesive is used for this purpose.

BRIEF DESCRIPTION OF THE DRAWING

FIG. 1 is an essentially schematic view illustrating a tubular knee support in accordance with the invention, shown applied to the knee of a user;

FIG. 2 is an isometric view depicting the inner surface of a blank used to form the knee support illustrated in FIG. 1;

FIG. 3 is a view illustrating the initial step of the manufacture of a knee support from the blank of FIG. 2, wherein the side margins of the blank are placed in opposition prior to taping of the resultant seam;

FIG. 4 is an elevational view of the completed knee support;

FIG. 5 is a fragmentary view of a blank in accordance with the invention, used in the fabrication of a leg prosthesis suspension device;

FIG. 6 is a view similar to that of FIG. 5, but depicting the completed suspension device;

FIG. 7 is a view similar to that of FIG. 2, but illustrating the use of a plurality of thin spaced apart bands of anti-slip material; and FIG. 8 is an enlarged sectional view taken along line 8—8 of FIG. 2 and illustrating the construction of the knee support.

DETAILED DESCRIPTION OF THE PREFERRED EMBODIMENT

Turning now to the drawings, and particularly FIGS. 2–4, a tubular knee support 10 (FIG. 2) is illustrated. The support 10 is in the form of an elongated, tubular body 12 presenting upper and lower opposed, open ends 14, 16. The body 12 includes an uppermost, diverging, somewhat frustoconical section 18 adapted to receive and conform with the lower thigh; a lower, arcuate in side elevation section 20 for receiving and conforming with the upper calf; and a central knee section 22. In addition, the support 10 includes a pair of anti-slip bands 24, 26 applied to the inner surface thereof adjacent each open end 14, 16.

The tubular body 10 is preferably formed of an inner layer 28 (see FIG. 8) of closed cell neoprene rubber synthetic resin material, which has sufficient softness, resiliency and strength for this purpose. As shown, the layer 28 is essentially continuous throughout its thickness and is substantially air-impervious. Normally, inner and outer surfaces of the neoprene rubber layer 28 are faced with fabric. In practice, use has been made of G-231-N and R-1400-N closed cell neoprene rubber sheeting commercialized by the Rubatex Corporation of Bedford, Va. The neoprene rubber is normally faced with stretched nylon 30 on the surface thereof which forms the exterior of the support 10; the opposed surface of layer 28 presenting the interior surface of the support 10 can be faced with stretch nylon or stretch Jersey fabric 32 (e.g., 900 standard light stretch Jersey commercialized by Rubatex Corporation). Rubatex brochures entitled "Closed Cell Rubber and Plastic Sheets", and "Neoprene/Stretch Jersey Laminates" which describe and characterize the neoprene rubber material and fabric facings are incorporated by reference herein.

The anti-slip bands 24, 26 are, in the present embodiment, continuous bands having a width of about ¾ to 1½". Advantageously, these bands are formed of IPOCON adhesive commercialized by IPOS N.A., Inc. of Niagara Falls, N.Y. This adhesive is a silicon-based synthetic resin material described as polydimethylsiloxane interlaced with fillers and acetoxysilan. This adhesive has been found to properly adhere to the inner surface of the support 10 and will not delaminate or erode during normal use. The bands 24, 26 can be applied by brush application of the viscous IPOCON adhesive or by any other acceptable technique. Normally, after application a cure time of at least 24 hours, and most preferably about 72 hours, is provided to insure adequate drying of the adhesive to form the anti-slip bands 24, 26.

It is also important that the anti-slip material of the invention be applied as a relatively thin layer, so as to not unduly limit the stretchability of the faced neoprene rubber material. Adequate stretchability is required, especially in the case of prosthesis suspension devices, in order to prevent a blood flow-restricting "tourniquet effect" which is especially troublesome for amputees because of restricted blood circulation at the area of the amputation. In practice, the anti-slip material should have a thickness of from about 0.0050–0.1 inches, and most preferably from about 0.01–0.05 inches. In the case of the bands 24, 26, a thickness of about 0.02 inches has been found to give very satisfactory results.

FIG. 2 illustrates a unitary one-piece blank 34 used in the fabrication of knee support 10. As illustrated, the bands 24, 26 are applied to the inner Jersey fabric 32 adjacent the opposed ends of the blank. In order to complete the construction, the transverse side margins of the blank 34 are brought together as illustrated in FIG. 3 to create an axially extending seam. This seam is completed by application of a length of seam tape. In particular, an adhesive material such as Rubatex R-27706 natural color adhesive is applied to the outer side margins of the blank 34. When these margins are brought into essentially abutting relationship as shown in FIG. 3, the seam tape is applied along the length of the seam in order to create the finished tubular support 10. The preferred details of the method of construction in seaming of the support 10 are set forth in U.S. Pat. No. 5,382,223 entitled "Contoured Orthopaedic Support Having Reduced Skin Irritation Properties"; such patent is incorporated by reference herein.

The use of support 10 is illustrated in FIG. 1, where it will be seen that the anatomically contoured support, together with anti-slip bands 24, 26, serve to maintain the position of the support even during strenuous exercise.

FIG. 7 illustrates a blank 34a which is identical with blank 34 except for the provision of differently configured anti-slip marginal bands 24a, 26a. In particular, each of these bands is formed of a plurality (here three) of thin strips of adhesive material with spacing between respective strips. Such a construction gives adequate anti-slip properties, but lessens the material requirements, as compared with the embodiment of FIGS. 1–4. All other construction techniques and material details are as described with reference to the first embodiment.

FIGS. 5–6 illustrate the construction of a leg prosthesis suspension device 36. Referring first to FIG. 5, it will be observed that a blank 38 is provided having a lower section 40 adapted to be interconnected to form a lower sleeve assembly 42. In addition, the upper portion of the blank 38 includes an elongated belt section 44 which is adapted to encircle the waist of a user. The outer end of belt 44 is provided with Velcro 46 which mates with an opposing Velcro section (not shown) on tab 48.

The blank 38 is formed of the same faced neoprene rubber material described with reference to support 10. Similarly, the lower margin of blank section 40 is provided with an anti-slip band 50 which is made from the described IPOCON adhesive. Finally, the sleeve portion 42 of the device 36 is formed in the same manner as support 10, i.e., an appropriate adhesive is applied to the side margins of the lower section 40 of the blank, and these are brought into abutment; a length of seam tape 52 is then applied along the exterior surface of the blank to complete the sleeve section 42.

In the use of device 36, the sleeve section 42 receives the stump of the user, and belt 44 is tightened around the user's waist. Thereafter, a leg prosthesis (not shown) is positioned adjacent the stump, with the anti-slip band 50 engaging the prosthesis. In this fashion, the prothesis is prevented from undesired shifting or slippage during use.

What is claimed is:

1. A sleeve assembly adapted to be worn on a limb and comprising:

a tubular body formed at least in part of resilient, stretchable synthetic resin material and presenting a longitudinal axis, opposed inner and outer surfaces, and upper and lower open ends, said body configured to fit over a limb with said inner surface proximal to the skin of the limb and with said limb extending through at least said upper open end, said body having a segment thereof for receiving anti-slip material, said segment being an integral part of said tubular body with said synthetic resin material extending continuously from said segment to the remainder of the body; and a synthetic resin anti-slip material applied to and supported by said segment on the inner surface thereof, said anti-slip material being located adjacent said upper open end of said tubular body and of elongated configuration and extending in a direction transverse to said tubular body longitudinal axis, said anti-slip material having a coefficient of static friction greater than that of said inner surface of said segment, said anti-slip material being initially applied to said inner surface as an uncured synthetic resin capable of directly bonding to said inner surface segment, and thereafter allowed to cure in place on said inner surface segment, said anti-slip material having a thickness less than the thickness of said body.

2. The sleeve assembly of claim 1, said anti-slip material being applied as an essentially continuous band adjacent one end of said body.

3. The sleeve assembly of claim 1, said anti-slip material being applied as a plurality of proximal, spaced apart bands.

4. The sleeve assembly of claim 1, said assembly being for leg prosthetic support and including a belt section integral with one end of said body and adapted to extend about the waist of a wearer.

5. The sleeve assembly of claim 1, said anti-slip material having a thickness of from about 0.005 to 0.1 inches.

6. The sleeve assembly of claim 1, said synthetic resin material forming said tubular body being neoprene rubber, there being stretch Jersey fabric applied to said material to form the inner surface of said body.

7. The sleeve assembly of claim 1, said anti-slip material being polydimethylsiloxane interlaced with acetoxysilane.

8. The sleeve assembly of claim 1, said anti-slip material applied to said segment inner surface solely through the adherence of said anti-slip material to said inner surface of said segment.

9. The sleeve assembly of claim 1, said anti-slip material being in the form of an elongated, continuous band.

* * * * *